US00PP16901P2

(12) United States Plant Patent
Dekker

(10) Patent No.: US PP16,901 P2
(45) Date of Patent: Aug. 1, 2006

(54) ***CHRYSANTHEMUM* PLANT NAMED 'EUROBELLE ROSY'**

(50) Latin Name: *Chrysanthemum×morifolium*
Varietal Denomination: Eurobelle Rosy

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 62 days.

(21) Appl. No.: 11/022,032

(22) Filed: Dec. 24, 2004

(51) Int. Cl.
*A01H 5/00* (2006.01)

(52) U.S. Cl. ..... Plt./291

(58) Field of Classification Search ..... Plt./291
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Eurobelle Rosy', characterized by its decorative-type inflorescences with elongated oblong-shaped, pink-colored ray florets; strong and upright flowering stems; freely flowering habit; early and uniform flowering response; and good postproduction longevity.

1 Drawing Sheet

Botanical designation: *Chrysanthemum×morifolium.*
Cultivar denomination: 'Eurobelle Rosy'.

BACKGROUND OF THE INVENTION

The present invention relates to a new and distinct cultivar of *Chrysanthemum* plant, botanically known as *Chrysanthemum×morifolium* and referred to by the name 'Eurobelle Rosy'.

The new *Chrysanthemum* is a naturally-occurring whole plant mutation of a proprietary selection of *Chrysanthemum×morifolium* identified as code number 96717,01/4, not patented. The new *Chrysanthemum* was discovered and selected by the Inventor on Dec. 21, 2002 as a single flowering plant within a population of plants of the parent selection in a controlled environment in Hensbroek, The Netherlands.

Asexual reproduction of the new *Chrysanthemum* by terminal cuttings in Hensbroek, The Netherlands since January, 2003, has shown that the unique features of this new *Chrysanthemum* are stable and reproduced true to type in successive generations.

BRIEF SUMMARY OF THE INVENTION

The cultivar Eurobelle Rosy has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Eurobelle Rosy'. These characteristics in combination distinguish 'Eurobelle Rosy' as a new and distinct cultivar:

1. Decorative-type inflorescences with elongated oblong-shaped, pink-colored ray florets; typically grown as a spray-type.
2. Strong and upright flowering stems.
3. Freely flowering habit.

4. Early and uniform flowering response.
5. Good postproduction longevity.

Plants of the new *Chrysanthemum* can be compared to plants of the parent selection. In side-by-side comparisons conducted in Hensbroek, The Netherlands, plants of the new *Chrysanthemum* differed from plants of the parent selection in the following characteristics:

1. Ray floret color of plants of the new *Chrysanthemum* was darker pink than ray floret color of plants of the parent selection.
2. Under high temperatures, ray floret color of plants of the new *Chrysanthemum* was more stable and resisted fading better than ray floret color of plants of the parent selection.

Plants of the new *Chrysanthemum* can be compared to plants of the *Chrysanthemum* cultivar Eurobelle, disclosed in U.S. Plant Pat. No. 12,659. In side-by-side comparisons conducted in Hensbroek, The Netherlands, plants of the new *Chrysanthemum* differed primarily from plants of the cultivar Eurobelle in the following characteristics:

1. Leaves of plants of the new *Chrysanthemum* were smaller and darker green in color than leaves of plants of the cultivar Eurobelle.
2. Plants of the new *Chrysanthemum* had shorter ray florets than plants of the cultivar Eurobelle.
3. Plants of the new *Chrysanthemum* and the parent selection differed in ray floret coloration as plants of the cultivar Eurobelle was white.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Eurobelle Rosy'.

The photograph at the bottom of the sheet comprises a close-up view of upper and lower surfaces of typical inflorescences and typical leaves of 'Eurobelle Rosy'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the summer and autumn in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5 to 30° C., night temperatures ranged from 18.5 to 24° C. and light levels were about five kilolux. Plants were pinched once and were about ten weeks from planting when the photographs and the description were taken.

Botanical classification: *Chrysanthemum×morifolium* cultivar Eurobelle Rosy.

Commercial classification: Decorative-type *Chrysanthemum* typically grown as a spray-type cut flower.

Parentage: Naturally-occurring whole plant mutation of a proprietary selection of *Chrysanthemum×morifolium* identified as code number 96717,01/4, not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine and freely branching; light brown in color.

Plant description:

*Appearance.*—Herbaceous decorative-type cut *Chrysanthemum*; typically grown as a spray-type; erect and strong flowering stems. Moderately vigorous.

*Flowering stem description.*—Length: About 70 to 80 cm. Diameter: About 6 mm. Strength: Strong. Texture: Pubescent. Aspect: Erect. Branching habit: Plants are typically grown as single stems. Color: 146B to 146C.

*Foliage description.*—Arrangement: Alternate. Length: About 9 to 14 cm. Width: About 5 to 8 cm. Apex: Acute. Base: Attenuate. Margin: Pinnately lobed. Texture, upper and lower surface: Pubescent; rough. Petiole length: About 1 to 4 cm. Color: Developing foliage, upper surface: 137A to 147A. Developing foliage, lower surface: 137B to 137C. Fully expanded foliage, upper surface: 137A to 137B. Fully expanded foliage, lower surface: 137C to 137D. Venation, upper and lower surfaces: 137D. Petiole, upper and lower surfaces: 137D.

Inflorescence description:

*Appearance.*—Decorative type inflorescence form with elongated oblong-shaped ray florets. Inflorescences borne on terminals above foliage. Disk and ray florets develop acropetally on a capitulum. Inflorescences not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 7.5 weeks later. Early and uniform flowering response.

*Postproduction longevity.*—Cut inflorescences will maintain good substance and form for about three weeks.

*Quantity of inflorescences per flowering stem.*—About 13 to 18 inflorescences per flowering stem.

*Inflorescence size.*—Diameter: About 5 to 7 cm. Depth (height): About 2 to 3 cm. Diameter of disc: About 3 mm.

*Inflorescence buds.*—Height: About 8 to 10 mm. Diameter: About 1 to 1.3 cm. Shape: Spherical. Color: 146A to 146B.

*Ray florets.*—Length: About 1.4 to 3.4 cm. Width: About 1 to 10 mm. Shape: Elongated oblong; incurving. Apex: Praemorse. Base: Fused; tubular. Margin: Entire. Texture, upper and lower surfaces: Smooth, glabrous. Number of ray florets per inflorescence: About 180 in numerous whorls. Color: When opening, upper and lower surfaces: 150D. Fully opened, upper surface: 69A to 69B; color becoming closer to 69B with development; towards the base, 145C. Fully opened, lower surface: Closest to 76D.

*Disc florets.*—Shape: Tubular; elongated. Length: About 5 mm. Width: About 1 to 2 mm. Number of disc florets per inflorescence: About 5. Color: Immature: 145A to 145B. Mature: Apex: 145A. Midsection: 155B. Base: 151C.

*Peduncles.*—Length, terminal peduncle: About 9 cm. Length, fourth peduncle: About 14 cm. Diameter: About 7 mm. Angle: About 60° from vertical. Strength: Moderately strong. Texture: Pubescent. Color: 137B to 137C.

*Reproductive organs.*—Androecium: Present on disc florets only. Anther color: 151B. Pollen color: 23A. Gynoecium: Present on both ray and disc florets. Stigma length: About 1 mm. Stigma diameter: About 0.3 mm. Stigma color: Towards the apex, 151B; towards the vase, 144C to 144D.

*Seed/fruit.*—Seed and fruit production has not been observed.

Disease/pest resistance: Resistance to known *Chrysanthemum* pathogens and pests has not been observed on plants of the new *Chrysanthemum*.

It is claimed:

1. A new and destinct cultivar of *Chrysanthemum* plant named 'Eurobelle Rosy', as illustrated and described.

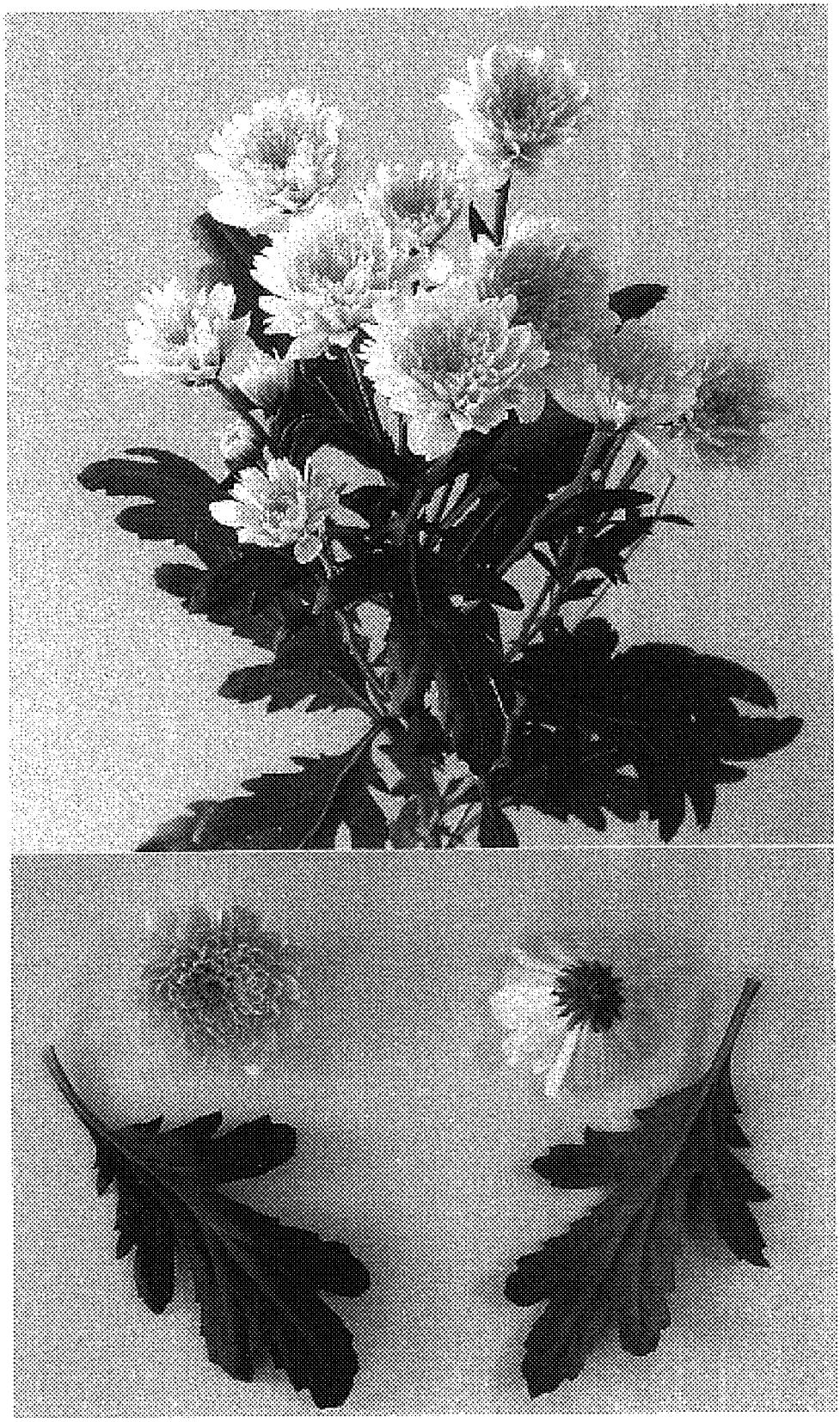

* * * * *